United States Patent
Bullard et al.

(10) Patent No.: US 9,839,225 B2
(45) Date of Patent: *Dec. 12, 2017

(54) METHOD FOR REDUCTION IN MICROBIAL ACTIVITY IN POULTRY PROCESSING

(71) Applicant: Zeco, Inc., Chattanooga, TN (US)

(72) Inventors: Jonathon R. Bullard, Chattanooga, TN (US); James A. Faller, Chattanooga, TN (US); Robert C. Bullard, Signal Mountain, TN (US)

(73) Assignee: Zeco, Inc., Chattanooga, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/237,862

(22) Filed: Aug. 16, 2016

(65) Prior Publication Data

US 2017/0042169 A1 Feb. 16, 2017

Related U.S. Application Data

(63) Continuation of application No. 14/945,698, filed on Nov. 19, 2015, now Pat. No. 9,414,609.

(Continued)

(51) Int. Cl.
*A01N 31/00* (2006.01)
*A23B 4/12* (2006.01)
(Continued)

(52) U.S. Cl.
CPC .............. *A23B 4/12* (2013.01); *A23B 4/0053* (2013.01); *A23L 3/3508* (2013.01); *A23V 2002/00* (2013.01)

(58) Field of Classification Search
CPC ....... A23B 4/12; A01N 37/16; A23V 2002/00
(Continued)

(56) References Cited

U.S. PATENT DOCUMENTS

| 2,512,640 A | 6/1950 | Greenspan et al. |
| 2,590,856 A | 4/1952 | Greenspan et al. |

(Continued)

FOREIGN PATENT DOCUMENTS

| GB | 947688 | 1/1964 |
| WO | WO 99/00025 | 1/1999 |

(Continued)

OTHER PUBLICATIONS

Bauerrneister et al., "Validating the Efficacy of Peracetic Acid Mixture as an Antimicrobial in Poultry Chillers", J. of Food Preotection, vol. 71, No. 6, 2008, pp. 1119-1122.

(Continued)

*Primary Examiner* — T. Victor Oh
(74) *Attorney, Agent, or Firm* — Patterson Thuente Pedersen, P.A.

(57) ABSTRACT

A process for reducing the bacterial count on a poultry carcass during poultry processing after the picking stage and prior to the chilling stage by applying an intervention solution having at least one equilibrium peroxycarboxylic acid or a pH modified peroxycarboxylic acid comprising peroxyacetic acid to the poultry carcass at an elevated temperature above 100° F. and at an elevated concentration of at least 200 ppm for a desired period of time of less than about 30 seconds to reduce the bacterial count by at least 60 percent. The process providing acceptable antimicrobial control in poultry processing prior to the chilling stage.

20 Claims, 1 Drawing Sheet

Related U.S. Application Data

(60) Provisional application No. 62/081,673, filed on Nov. 19, 2014.

(51) Int. Cl.
*A23L 3/3508* (2006.01)
*A23B 4/005* (2006.01)

(58) Field of Classification Search
USPC .......................................................... 514/714
See application file for complete search history.

(56) References Cited

U.S. PATENT DOCUMENTS

| | | |
|---|---|---|
| 2,609,391 A | 9/1952 | Greenspan et al. |
| 2,735,777 A | 2/1956 | Meyer |
| 3,122,417 A | 2/1964 | Blaser et al. |
| 3,934,044 A | 1/1976 | Busch et al. |
| 4,051,058 A | 9/1977 | Böwing et al. |
| 4,051,059 A | 9/1977 | Böwing et al. |
| 4,297,298 A | 10/1981 | Crommelynck et al. |
| 4,743,447 A | 5/1988 | Le Rouzic et al. |
| 4,766,646 A | 8/1988 | Parker |
| 4,770,884 A | 9/1988 | Hill et al. |
| 4,790,943 A | 12/1988 | Dunn et al. |
| 4,849,237 A | 7/1989 | Hurst |
| 4,852,216 A | 8/1989 | Clayton et al. |
| 4,865,855 A | 9/1989 | Hansen et al. |
| 4,999,202 A | 3/1991 | Cronje et al. |
| 5,053,140 A | 10/1991 | Hurst |
| 5,069,922 A | 12/1991 | Brotsky et al. |
| 5,093,140 A | 3/1992 | Watanabe |
| 5,139,788 A | 8/1992 | Schmidt |
| 5,143,739 A | 9/1992 | Bender et al. |
| 5,173,190 A | 12/1992 | Picek |
| 5,178,755 A | 1/1993 | LaCrosse |
| 5,178,890 A | 1/1993 | Van den Nieuwelaar et al. |
| 5,200,189 A | 4/1993 | Oakes et al. |
| 5,208,057 A | 5/1993 | Greenley et al. |
| 5,234,703 A | 8/1993 | Guthery |
| 5,314,687 A | 5/1994 | Oakes et al. |
| 5,350,563 A | 9/1994 | Kralovic et al. |
| 5,364,650 A | 11/1994 | Guthery |
| 5,409,713 A | 4/1995 | Lokkesmoe et al. |
| 5,427,868 A | 6/1995 | Bringley et al. |
| 5,435,808 A | 7/1995 | Holzhauer et al. |
| 5,489,434 A | 2/1996 | Oakes et al. |
| 5,593,598 A | 1/1997 | McGinness et al. |
| 5,632,676 A | 5/1997 | Kurschner et al. |
| 5,635,231 A | 6/1997 | Bender et al. |
| 5,728,305 A | 3/1998 | Hawkinson |
| 6,010,729 A | 1/2000 | Gutzmann et al. |
| 6,103,286 A | 8/2000 | Gutzmann et al. |
| 6,113,963 A | 9/2000 | Gutzmann et al. |
| 6,183,807 B1 | 2/2001 | Gutzmann et al. |
| 6,514,556 B2 | 2/2003 | Hilgren et al. |
| 6,534,075 B1 | 3/2003 | Hei et al. |
| 6,545,047 B2 | 4/2003 | Gutzmann et al. |
| 6,627,593 B2 | 9/2003 | Hei et al. |
| 6,627,657 B1 | 9/2003 | Hilgren et al. |
| 6,674,538 B2 | 1/2004 | Takahashi |
| 6,767,569 B1 | 7/2004 | Marsden et al. |
| 6,828,294 B2 | 12/2004 | Kellar et al. |
| 6,865,895 B2 | 3/2005 | Bass |
| 6,964,788 B2 | 11/2005 | Phebus et al. |
| 7,077,967 B2 | 7/2006 | Perkins et al. |
| 7,754,670 B2 | 7/2010 | Lange et al. |
| 7,887,641 B2 | 2/2011 | Man et al. |
| 8,020,520 B2 | 9/2011 | Hilgren et al. |
| 8,029,693 B2 | 10/2011 | Dada et al. |
| 8,030,351 B2 | 10/2011 | Gutzmann et al. |
| 8,043,650 B2 | 10/2011 | Gutzmann et al. |
| 8,057,812 B2 | 11/2011 | Man et al. |
| 8,128,976 B2 | 3/2012 | Man et al. |
| 8,372,461 B2 | 2/2013 | Bullard et al. |
| 9,414,609 B1 * | 8/2016 | Bullard ................ A23B 4/20 |
| 2003/0070691 A1 | 4/2003 | Giletto et al. |
| 2003/0148727 A1 | 8/2003 | Hilgren et al. |
| 2003/0211169 A1 | 11/2003 | Tabasso |
| 2006/0113506 A1 | 6/2006 | Man et al. |
| 2007/0269536 A1 | 11/2007 | Bailey et al. |
| 2008/0171117 A1 | 7/2008 | Mixon et al. |
| 2009/0043123 A1 | 2/2009 | Copenhafer et al. |
| 2009/0145859 A1 | 6/2009 | Man et al. |
| 2009/0147822 A1 | 6/2009 | Tokhtuev et al. |
| 2009/0324790 A1 | 12/2009 | Hilgren et al. |
| 2010/0021557 A1 | 1/2010 | Li et al. |
| 2010/0196503 A1 | 8/2010 | Heisig et al. |
| 2010/0227000 A1 | 9/2010 | Ames et al. |
| 2011/0027383 A1 | 2/2011 | Hilgren et al. |
| 2011/0135534 A1 | 6/2011 | Bates et al. |
| 2011/0177145 A1 | 7/2011 | Erkenbrecher, Jr. et al. |
| 2011/0220155 A1 | 9/2011 | Man et al. |
| 2011/0274766 A1 | 11/2011 | Allen et al. |
| 2011/0305805 A1 | 12/2011 | Gutzmann et al. |
| 2011/0311691 A1 | 12/2011 | Gutzmann et al. |
| 2012/0244261 A1 | 9/2012 | Harvey et al. |
| 2012/0245228 A1 | 9/2012 | Harvey et al. |
| 2012/0322872 A1 | 12/2012 | Kraus et al. |

FOREIGN PATENT DOCUMENTS

| | | |
|---|---|---|
| WO | WO 00/48951 | 8/2000 |
| WO | WO 02/054866 A1 | 7/2002 |
| WO | WO 2009/027857 A1 | 3/2009 |

OTHER PUBLICATIONS

Bell, "Reduction of doodborne micro-organisms on beef carcass tissue using acetic acid, sodium bicarbonate, and hydrogen peroxide spray washes", Food Microbiology, 1997, 14, pp. 439-448.

Carciofi et al, "Water uptake by poultry carcasses during cooling by water immersion", Chemical Engineering and Processing: Process Intensification, vol. 46, No. 5, 2007, pp. 444-450.

Dorn, "Examination of *Salmonella* Decontamination of Broiler Carcasses", 1988, 28 pages, both German and English languages.

Georgia FoodPac Food Processing Advisory Council, Georgia's Traditional Industries Program for Food Processing—Fiscal Year 2004-2005 Report to Industry, 24 pages.

Gusev, "Peracetic Acid for *Salmonella* Decontamination in Poultry Carcasses", Veterinary Disease Control Review, 2007, 4 pages.

Harris et al., "Microbilogical and organoleptic characteristics of beef trim and ground beef treated with acetic acid, lactic acid, acidified sodium chlorite, or sterile water in a simulated commercial processing environment to reduce *Escherichia coli* O157:H7 and *Almonella*", Meat Science, 90, 2012, pp. 783-788.

Joseph, "Meat Decontamination", University of Bristol, 1997, pp. 1, 8-9, 12, 33-35, 38, 43, 64-91, 98-99 and 104-105.

Labadie, "Development of a New Technique for Obtaining Axenic Meat", European J. Appl. Microbiol., 1977, 4, 67-73.

Mohan et al. "Role of Peroxyacetic Acid, Octanoic Acid, Malic Acid, and Potassium Lactate on the Microbiological and Instrumental Color Characteristics of Ground Beef", J. Food Science, vol. 77, No. 4, 2012, pp. M188-M193.

Quilo et al., "Microbial, instrumental color and sensory characteristics of inoculated ground beef produced using potassium lactate, sodium metasilicate or peroxyacetic acid as multiple antimicrobial interventions", Meat Science, 84, 2010, pp. 470-476.

Rose, "USDA Policy on Water Reuse in Meat and Poultry Plants", American Meat Science Association, 45th Reciprocal Meat Conference, vol. 45, 1992, pp. 147-149.

Russell, "Solving the Yield/Pathogen Reduction Dilemma", Watt 290 Poultry USA, Oct. 2007, pp. 30-34.

Russell, "Water Reuse in Poultry Processing Now Addressed in the HACCP Program", The University of Georgia Cooperative Extension, Jan. 2013, 4 pages.

Saravia et al., "Economic Analysis of Recycling Chiller Water in Poultry-Processing Plants Using Ultrafiltration Membrane Systems", J. Food Distribution Research, 36(1):161-166, Mar. 2005.

(56) References Cited

OTHER PUBLICATIONS

Application and File history for U.S. Appl. No. 12/911,539, filed Oct. 25, 2010. Inventors: Bullard et al.
Application and File history for U.S. Appl. No. 13/764,199, filed Feb. 11, 2013. Inventors: Bullard et al.
Application and File history for U.S. Appl. No. 14/467,603, filed Aug. 25, 2014. Inventors: Bullard et al.
Application and File history for U.S. Appl. No. 14/945,698, filed Nov. 19, 2015. Inventors: Bullard et al.

* cited by examiner

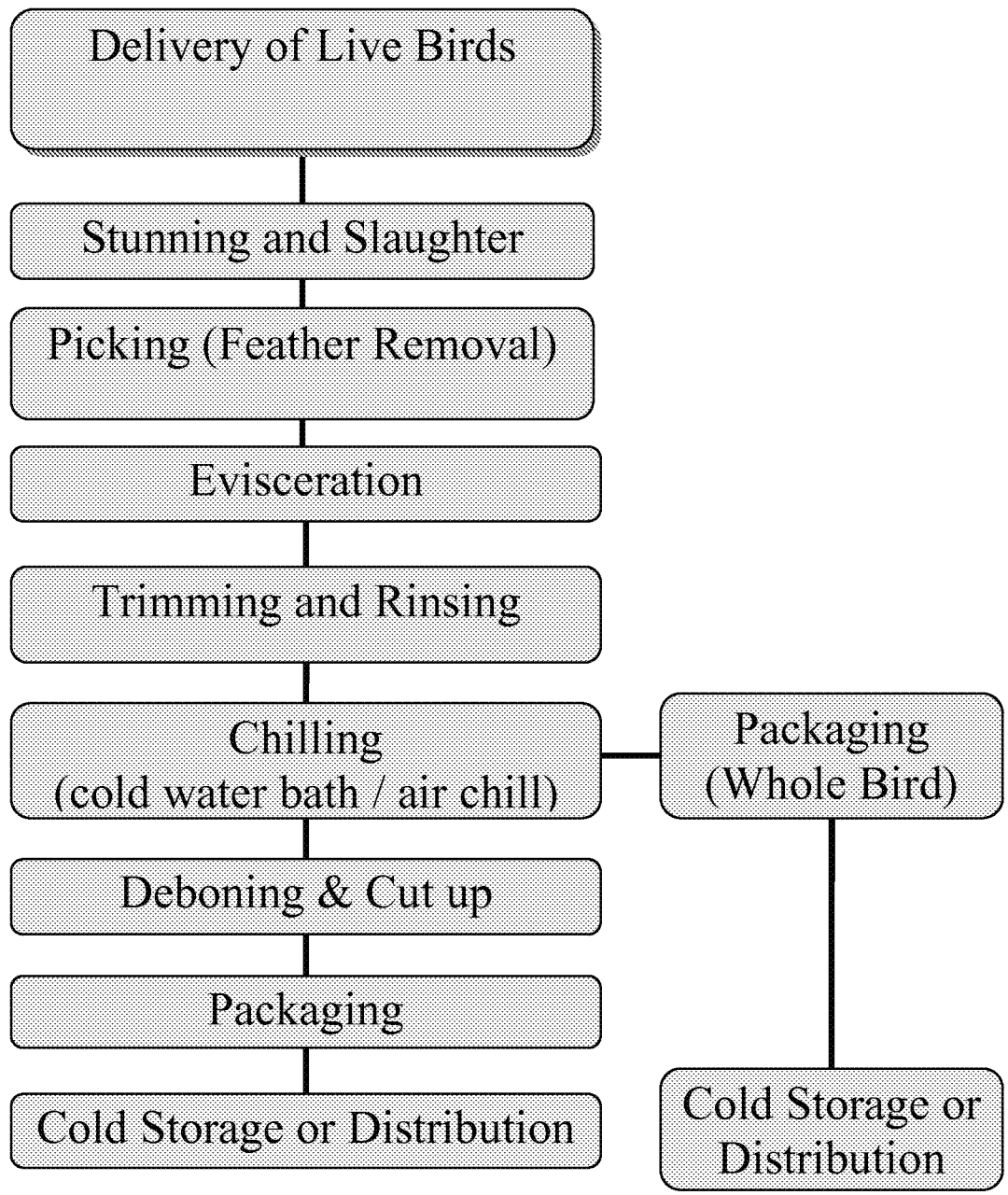

METHOD FOR REDUCTION IN MICROBIAL ACTIVITY IN POULTRY PROCESSING

RELATED APPLICATION

This application is a continuation of application Ser. No. 14/945,698, filed Nov. 19, 2015, now U.S. Pat. No. 9,414,609, issued Aug. 16, 2016, which claims the benefit of U.S. Provisional Application No. 62/081,673, filed Nov. 19, 2014, each of which is hereby fully incorporated herein by reference.

FIELD OF THE INVENTION

The present invention relates to a method of reducing the bacterial count on a poultry carcass during poultry processing by exposing the poultry carcass to a solution comprising a peroxycarboxylic acid at an elevated concentration and temperature, more particularly soaking, dipping, quenching, rinsing and/or washing the poultry carcass after the bleed out stage and prior to immersion chilling stage in a solution comprising a peroxycarboxylic acid at an elevated concentration and temperature, the peroxycarboxylic acid preferably comprising peroxyacetic acid, and more particularly an equilibrium peroxycarboxylic acid solution, and more preferably a pH modified peroxycarboxylic acid solution.

BACKGROUND OF THE INVENTION

The world population has grown to point where mass production of the foods that we consume is no longer a luxury but a requirement. Local farmers, providing food and food products directly to the marketplace, cannot meet the demands of modern society. The food supply chain now incorporates very large, complex farms and high speed and very high volume processing plants to satisfy the need for mass processing and production of food. Maintaining a safe food supply chain relies on the dedication of those working in the supply chain, the processing plants and also on the third party oversight of various Federal agencies whose regulations support and mandate food safety.

With two major exceptions, the physical process of taking an animal from the farm to the consumer has changed very little over time. The introduction of refrigeration, and the implementation of various chemistries to help maintain sanitary conditions and to control microbiology, has given modern food processors an advantage not enjoyed by food producers of a century ago. Refrigeration and chemical intervention practices have become an integral part of food processing facility operations. These technologies have enabled the high speed, high volume output of the large processing facilities that could not have been possible in times past without significant concern for consumer safety. With large scale and continuous processing methods being employed by large processors of protein products, or any other product that is susceptible to microbiological contamination, the concern for the control of microbiology and the safety of the food supply chain is of paramount importance.

Another concern, as the demand for food products increases, is the impact on natural resources created by this demand. The ecological impact is directly affected by this growth and therefore new processes must be developed to reduce the impact any given process has on the environment. The ecological impact that a food processing plant has on the environment is no longer a passing concern but a major part of operations and planning. Entire processes are built around the control and conservation of natural resources such as water. Older, outdated and less efficient processes are being replaced at significant cost with more efficient and less wasteful processes that maximizes the utility of available resources. No longer can a plant operate without concern for the conservation and sustainability of natural resources. As each step in food processing becomes more efficient, the natural resources required to be used in subsequent steps can be minimized to conserve and sustain our natural resources.

Still another concern in slaughtering and processing plants is unwanted microorganisms that are emitted into the air or are contained on the animal carcass when the animal is processed, such as poultry (i.e., turkey, duck and chicken) during shackling, killing, scalding, and picking areas. The microorganisms that may become airborne or contained on the animal carcass are unwanted in the processing and packing areas of the plant because they can affect product quality and safety. They also pose a potential threat to the health and well-being of the workers in the plant. Still further, such microorganisms can affect down-field processes in a processing plant, posing quality and safety concerns to the ultimate consumer of the poultry product.

To insure that the food supply chain in modern society is maintained at the highest levels of safety for the consumer, the plant's employees, and the overall environment, there are federal agencies that monitor the processors operations so that a continually safe food supply is assured and the environmental impact and utilization of natural resources is as safe and efficient as possible. Modern food processing methods are scrutinized by government agencies to ensure compliance with safe handling and processing guidelines designed to minimize issues of food safety in the supply chain Regulations and routine inspections of systems and processes by Federal agencies such as the USDA, EPA and OSHA, mandate a government-industry alliance that helps ensure that every effort is made to deliver the safest food product possible to the consumer.

Very innovative approaches to the systems and methods used in processing facilities have been implemented to create profits for industry while maintaining low consumer cost of the final product. As new processes are developed, the federal agencies that have jurisdiction over any particular process are called upon to review the new approach and to ensure that the new innovation meets the current guidelines for safety. The higher the processors output, the higher the risk of microbiological contamination, and therefore the more innovative the processor must be to combat this ever present threat to the food chain safety. As new risks are found, federal guidelines become more stringent.

Large scale refrigeration systems, used to help control microbial growth in various processing applications, have helped the food processing industry to remain in compliance with food safety goals. Refrigeration applications and processes are implemented at various locations in the processing operation to ensure maximization of microbiology control and shelf life. Depending on the particular product being processed—beef, pork, poultry and fish for example—and the particular operation taking place, various methods of achieving this reduction in product temperature are employed. In industrial processing of poultry, for example, immediately after slaughter, bleed out, hot water immersion, feather removal and viscera withdrawal, poultry carcasses have to be chilled to reduce their temperature from approximately 40° C. to 4° C., which contributes to food safety. While poultry carcasses may undergo air chilling after evisceration, in countries such as the United State and Brazil, two of the biggest poultry producers in the world, poultry carcasses usually undergo immersion chilling after evisceration by submersing the poultry carcass in large chilled water bath tanks.

Immersion chilling has a benefit of an increased "washing effect" which lowers the total microbial load on the birds; however, it is also a potential place for cross contamination to occur. In order to control microbiology in chiller tanks, it is a typical practice to add specialized chemistry to the tanks throughout the processing day. This specialized chemistry, known in the industry as intervention solutions kill or provide a $\log_{10}$ reduction in the amount of any unwanted microorganisms. There are several antimicrobials that are approved and effective for use in the chiller to decrease pathogens, including, for instance, chlorine, peroxyacetic acid ("PAA"), CPC, organic acids, TSP, acidified sodium chlorite and chlorine dioxide. Because chiller tanks are often quite voluminous, the amount of antimicrobials needed can be quite high to provide a desired $\log_{10}$ reduction in the amount of any unwanted microorganisms.

PAA, which is also sometimes called peroxyacetic acid, is a peroxycarboxylic acid and is a well known chemical for its strong oxidizing potential, has the molecular formula $CH_3COOOH$, and has a molecular structure as follows:

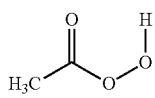

An equilibrium peroxyacetic acid solution is produced from an equilibrium mixture of hydrogen peroxide, acetic acid and water ("equilibrium PAA solution"), which often uses an acid catalyst, e.g., sulfuric acid.

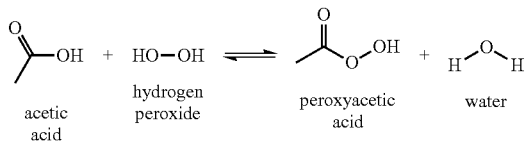

U.S. Pat. No. 5,632,676, which pertains to the application of equilibrium PAA solutions to fowl at an application concentration of about 100 ppm to about 2000 ppm, discloses such equilibrium solutions having a pH around 3.

Beyond equilibrium PAA solutions, other equilibrium peroxycarboxylic acid ("PCA") solutions can also be produced from a similar equilibrium mixture of hydrogen peroxide, water and the respective acid. Such commercial products also often contain stabilizers and/or catalysts, like 1 Hydroxyethylidene 1-1 diphosphonic acid (HEDP), various phosphate salts, organic or inorganic acids, etc., to facilitate production and storage stability of the product. Hydrogen peroxide is always present in excess in the natural equilibrium formulation of PAA solutions (and other equilibrium PCA solutions).

As such, there is a need in the industry to efficiently and cost-effectively reduce microbial contamination of poultry carcasses during poultry processing. There is also a need in the industry to efficiently and cost-effectively minimize the amount of unwanted microorganisms on a poultry carcass during processing prior to the immersion chilling step.

SUMMARY OF THE INVENTION

In some aspects of the present invention, a method for the reduction in microbial activity in protein food products intended for human consumption comprises contacting the protein food products with a solution comprising a peroxycarboxylic acid at an elevated concentration and elevated temperature for a desired period of time.

In some aspects of the present invention, the method for the reduction in microbial activity in protein food products intended for human consumption comprises contacting a poultry carcass and/or poultry parts with a solution comprising a peroxycarboxylic acid at an elevated concentration and elevated temperature for a desired period of time. While the following disclosure refers to a poultry carcass, it should be appreciated that the disclosure is equally applicable to more than one poultry carcass, as well as one or more poultry parts.

In some aspects, the poultry carcass is soaked, dipped, quenched, rinsed and/or washed after the bleed-out stage and prior to the chilling stage in a solution comprising a peroxycarboxylic acid at an elevated concentration and elevated temperature for a desired period of time. In some aspects, the peroxycarboxylic acid comprises between about 2 to 12 carbon atoms, and in some aspects comprises peroxyacetic acid. In some aspects, the poultry carcass is soaked, dipped, quenched, rinsed and/or washed after the picking stage. In some aspects, the peroxycarboxylic acid is an equilibrium peroxycarboxylic acid solution, while in some other aspects the peroxycarboxylic acid is a pH modified peroxycarboxylic acid solution.

In some aspects, the poultry carcass has a temperature of about 40° C. after the picking stage and prior to the soaking, dipping, quenching, rinsing and/or washing in a solution comprising a peroxycarboxylic acid at an elevated concentration and elevated temperature for a desired period of time according to certain aspects of the present invention.

In some aspects, the poultry carcass has a temperature greater than about 4° C. after the soaking, dipping, quenching, rinsing and/or washing in a solution comprising a peroxycarboxylic acid at an elevated concentration and elevated temperature for a desired period of time according to certain aspects of the present invention and prior to the chilling stage.

In some other aspects, the poultry carcass after the bleed-out stage and prior to the chilling stage has a temperature less than about 40° C. and greater than about 4° C. In still other aspects, the poultry carcass has a temperature greater than about 4° C. and less than about 40° C. prior to the soaking, dipping, quenching, rinsing and/or washing in a solution comprising a peroxycarboxylic acid at an elevated concentration and elevated temperature for a desired period of time according to certain aspects of the present invention.

In some aspects, the poultry carcass is soaked, dipped, quenched, rinsed and/or washed in an intervention solution after the bleed-out stage and prior to the chilling stage, said intervention solution at an elevated temperature and elevated concentration for desired period of time, wherein said elevated concentration of the intervention solution is between about 200 ppm and about 5000 ppm, in some aspects between about 300 ppm and about 2500 ppm, in some aspects between about 350 ppm and about 1500 ppm, in some aspects between about 400 ppm and about 1000 ppm, and in some other aspects between about 500 ppm and about 750 ppm. In some other aspects, said elevated concentration of the intervention solution is between about 300 ppm and about 5000 ppm, in some aspects between about 400 ppm and about 2500 ppm, in some aspects between about 500 ppm and about 2000 ppm, in some aspects between about 500 ppm and about 1000 ppm, and in some other aspects between about 500 ppm and about 700 ppm.

In some aspects, the poultry carcass is soaked, dipped, quenched, rinsed and/or washed in an intervention solution after the bleed-out stage and prior to the chilling stage, said intervention solution at an elevated temperature and elevated concentration for desired period of time, wherein the intervention solution comprises an equilibrium peroxycarboxylic acid. In some aspects, the equilibrium peroxycarboxylic acid has a pH above about 3.0 and below about 7.0, in certain aspects a pH range of about 3.5 to about 5.5, and in some other aspects a pH range of about 3.5 to about 5.0. In certain preferred aspects of the present invention, the equilibrium peroxycarboxylic acid comprises peroxyacetic acid.

In some aspects, the poultry carcass is soaked, dipped, quenched, rinsed and/or washed in an intervention solution after the bleed-out stage and prior to the chilling stage, said intervention solution at an elevated temperature and elevated concentration for desired period of time, wherein the intervention solution comprises a pH modified peroxycarboxylic acid. In some aspects, the pH modified peroxycarboxylic acid has a pH above about 7.0 and below about 10.0, in certain aspects a pH range of about 7.0 to about 9.5, and in some other aspects a pH range of about 7.5 to about 9.0. In certain preferred aspects of the present invention, the pH modified peroxycarboxylic acid comprises peroxyacetic acid.

In certain aspects of the present invention, the pH modified peroxycarboxylic acid is prepared using at least one buffering agent, said at least one buffering agent chosen from sodium hydroxide, potassium hydroxide, sodium salts of carbonic acid, potassium salts of carbonic acid, phosphoric acid, silicic acid and combinations thereof.

In some aspects, the poultry carcass is soaked, dipped, quenched, rinsed and/or washed in an intervention solution after the bleed-out stage and prior to the chilling stage, wherein said intervention solution at an elevated temperature and elevated concentration for a desired period of time, wherein the elevated temperature is between about 100° F. and about 150° F., in certain aspects between about 110° F. and about 140° F., in certain aspects between about 115° F. and about 135° F., in certain aspects between about 120° F. and about 130° F., and in certain aspects between about 122° F. and about 128° F. In some other aspects, said elevated temperature is between about 110° F. and about 150° F., in certain aspects between about 115° F. and about 140° F., in certain aspects between about 120° F. and about 135° F., in certain aspects between about 125° F. and about 130° F., and in certain aspects between about 120° F. and about 128° F.

In some aspects, the poultry carcass is soaked, dipped, quenched, rinsed and/or washed in an intervention solution after the bleed-out stage and prior to the chilling stage, said intervention solution at an elevated temperature and elevated concentration for a desired period of time to result in at least a 60% bacterial count reduction, in some aspects at least a 70% bacterial count reduction, in some aspects at least an 80% bacterial count reduction, and in some aspects at least a 90% bacterial count reduction, wherein the desired period of time is in the range of greater than 0 seconds to about 30 seconds, in certain aspects between about 1 second and about 20 seconds, in certain aspects between about 2 seconds and about 15 seconds, in certain aspects between about 3 seconds and about 10 seconds, and in certain aspects between about 4 seconds and about 8 seconds. In some other aspects, the desired period of time is between about 1 second and about 30 seconds, in certain aspects between about 2 seconds and about 20 seconds, in certain aspects between about 3 seconds and about 15 seconds, and in certain aspects between about 3 seconds and about 10 seconds.

In some aspects, the poultry carcass is soaked, dipped, quenched, rinsed and/or washed in an intervention solution after the picking stage and prior to an immersion chilling stage, said intervention solution at an elevated temperature and an elevated concentration for a desired period of time, wherein said intervention solution comprises a pH modified peroxyacetic acid solution having a pH between about 7.0 and 9.5, said elevated temperature being between about 115° F. and about 135° F., said elevated concentration being between about 500 ppm and about 750 ppm of said pH modified peroxyacetic acid, and said desired period of time being between about 2 seconds and 10 seconds to result in at least a 60% bacterial count reduction, in some aspects at least a 70% bacterial count reduction, in some aspects at least an 80% bacterial count reduction, in some aspects at least a 90% bacterial count reduction, and in some aspects at least a 95% bacterial count reduction.

In some aspects, after application of the intervention solution to the poultry carcass at an elevated temperature and an elevated concentration for a desired period of time according to certain aspects of the present invention, the poultry carcass is chilled to reduce the temperature to about 4° C.

In some aspects of the present invention, the intervention solution is rinsed off the carcass and/or parts with water after the desired application period of time. In some aspects of the present invention, the intervention solution is rinsed off the carcass and/or parts with water after the desired application period of time prior to immersion chilling. In some aspects of the present invention, after the intervention solution is applied, it is not subsequently rinsed off the carcass and/or parts at the processing plant, such that the intervention solution is allowed to be left on the poultry carcass and/or parts until the immersion chilling stage.

In some aspects, the peroxycarboxylic acid solution is chosen from peroxyformic, peroxypropionic, peroxyacetic, peroxybutanoic, peroxypentanoic, peroxyhexanoic, peroxyheptanoic, peroxyoctanoic, peroxynonanoic, peroxydecanoic, peroxyundecanoic, peroxydodecanoic, peroxylactic, peroxymaleic, peroxyascorbic, peroxyhydroxyacetic, peroxyoxalic, peroxymalonic, peroxysuccinic, peroxyglutaric, peroxyadipic, peroxypimelic, peroxysubric acid, and mixtures thereof.

The above summary is not intended to describe each illustrated embodiment or every implementation of the subject matter hereof.

BRIEF DESCRIPTION OF THE DRAWINGS

FIG. 1 is a flow diagram of poultry processing, with the reduction of the bacterial count on a poultry carcass according to certain aspects of the present invention occurring between the picking and chilling stages.

DETAILED DESCRIPTION OF THE DRAWINGS

As illustrated in the flow diagram of FIG. 1, normally meat poultry processing is initiated by hanging, or shackling, the birds to a processing line after being transferred from coops or transport cages. After the stunning, bleeding and scalding stages, the bird typically undergoes a picking stage where the feathers are removed from the carcass using an automated picker machine. Prior to the chilling stage, the feet, head, neck, oil glands and internal organs can be removed from the carcass; and the can carcass be washed and cleaned for microbial (i.e., *E. coli, Campylobacter, Salmonella*) and visible concerns.

In the present invention, the inventors have surprisingly discovered that after the bleed-out stage, and in some embodiments after the picking stage, and prior to the chilling stage, contacting the poultry carcass with an intervention solution comprising a peroxycarboxylic acid at an elevated temperature and at an elevated concentration for a desired period of time can unexpectedly reduce a bacterial count by as much as 80 percent or more. This reduction of bacterial count after the picking stage and prior to the chilling stage is beneficial to the down-line processes in a processing plant, helping to improve quality and minimizing safety concerns relating to microbial contamination of the poultry product. The peroxycarboxylic acid in some embodiments comprises an equilibrium peroxycarboxylic acid while in some other embodiments comprises a pH modified peroxycarboxylic acid.

The intervention solution preferably comprises at least one peroxycarboxylic acid having between 2 and 12 carbon atoms, the peroxycarboxylic acid being chosen from peroxyformic acid, peroxypropionic acid, peroxyacetic acid, peroxybutanoic acid, peroxypentanoic acid, peroxyhexanoic acid, peroxyheptanoic acid, peroxyoctanoic acid, peroxynonanoic acid, peroxydecanoic acid, peroxyundecanoic acid, peroxydodecanoic acid, peroxylactic acid, peroxymaleic acid, peroxyascorbic acid, peroxyhydroxyacetic acid, peroxyoxalic acid, peroxymalonic acid, peroxysuccinic acid, peroxyglutaric acid, peroxyadipic acid, peroxypimelic acid, peroxysubric acid, and mixtures thereof. Preferably, the intervention solution comprises an equilibrium peroxyacetic acid or a pH modified peroxyacetic acid.

The equilibrium peroxyacetic acid preferably has a pH above about 3.0 and below about 7.0, in some aspects about 3.5 to about 5.5, and in some other aspects about 3.5 to about 5.0, although subranges within these ranges is contemplated.

The pH modified peroxycarboxylic acid preferably has a pH above about 7.0 and below about 10.0, in certain aspects a pH range of about 7.0 to about 9.5, and in some other aspects a pH range of about 7.5 to about 9.0, although subranges within these ranges is contemplated. The pH modified peroxycarboxylic acid can be prepared by combining a peroxycarboxylic acid solution, such as a peroxyacetic acid solution, with one or more buffering agents chosen from sodium hydroxide, potassium hydroxide, the sodium salt of carbonic acid, the potassium salt of carbonic acid, phosphoric acid, silicic acid or mixtures thereof, in a quantity that is necessary to bring the solution to said pH range. One of ordinary skill in the art will appreciate that other alkalizing chemistries approved for direct food contact may also be used, whether alone or in combination with any of the foregoing buffering agents. The quantity of the buffering agent in a buffered peroxycarboxylic acid solution will generally be in the range of about 0.01% to about 10% by volume of the total solution, but other volumes of the buffering agent may be utilized depending upon various parameters, such as local water condition, including pH, hardness and conductivity.

In some aspects, the poultry carcass has a temperature of about 40° C. after the picking stage and prior to the soaking, dipping, quenching, rinsing and/or washing in a solution comprising a peroxycarboxylic acid at an elevated concentration and elevated temperature for a desired period of time. In some aspects, the poultry carcass has a temperature of about 30° C. to about 42° C., in some aspects about 30° C. to about 40° C., and in some other aspects about 35° C. to about 40° C., after the picking stage and prior to the soaking, dipping, quenching, rinsing and/or washing in a solution comprising a peroxycarboxylic acid at an elevated concentration and elevated temperature for a desired period of time. In some other aspects, the poultry carcass has a temperature greater than about 4° C. after the soaking, dipping, quenching, rinsing and/or washing in a solution comprising a peroxycarboxylic acid at an elevated concentration and elevated temperature for a desired period. In still some other aspects, the poultry carcass has a temperature greater than about 4° C. and less than about 40° C. prior to the soaking, dipping, quenching, rinsing and/or washing in a solution comprising a peroxycarboxylic acid at an elevated concentration and elevated temperature for a desired period of time.

The elevated temperature of the equilibrium peroxycarboxylic acid or pH modified peroxycarboxylic acid applied to the poultry carcass is between about 100° F. and about 150° F., in certain aspects between about 110° F. and about 140° F., in certain aspects between about 115° F. and about 135° F., in certain aspects between about 120° F. and about 130° F., and in certain aspects between about 122° F. and about 128° F., with other subranges within the foregoing ranges contemplated. In some other aspects, said elevated temperature is between about 110° F. and about 150° F., in certain aspects between about 115° F. and about 140° F., in certain aspects between about 120° F. and about 135° F., in certain aspects between about 125° F. and about 130° F., and in certain aspects between about 120° F. and about 128° F.

The equilibrium peroxycarboxylic acid or the pH modified peroxycarboxylic acid solution, or buffered peroxycarboxylic acid solution, contains the peroxycarboxylic acid and/or its conjugate salt applied to the poultry carcass in an elevated concentration range between about 200 ppm and about 5000 ppm, in some aspects between about 300 ppm and about 2500 ppm, in some aspects between about 350 ppm and about 1500 ppm, in some aspects between about 400 ppm and about 1000 ppm, and in some other aspects between about 500 ppm and about 750 ppm, with other subranges within the foregoing ranges contemplated. In some other aspects, said elevated concentration of the intervention solution is between about 300 ppm and about 5000 ppm, in some aspects between about 400 ppm and about 2500 ppm, in some aspects between about 500 ppm and about 2000 ppm, in some aspects between about 500 ppm and about 1000 ppm, and in some other aspects between about 500 ppm and about 700 ppm.

In certain other aspects of the present invention, the equilibrium peroxycarboxylic acid or the pH modified peroxycarboxylic acid solution comprises peroxyacetic acid in an elevated concentration range between 200 ppm and about 5000 ppm, in some aspects between about 300 ppm and about 2500 ppm, in some aspects between about 350 ppm and about 1500 ppm, in some aspects between about 400 ppm and about 1000 ppm, and in some other aspects between about 500 ppm and about 750 ppm. In some other aspects, said elevated concentration of the intervention solution is between about 300 ppm and about 5000 ppm, in some aspects between about 400 ppm and about 2500 ppm, in some aspects between about 500 ppm and about 2000 ppm, in some aspects between about 500 ppm and about 1000 ppm, and in some other aspects between about 500 ppm and about 700 ppm.

The intervention solution after the picking stage and prior to the chilling stage is applied to the poultry carcass for a desired period of time to result in at least a 60% bacterial count reduction on said poultry carcass, in some aspects at least a 70% bacterial count reduction on said poultry carcass, in some aspects at least an 80% bacterial count reduction on said poultry carcass, in some aspects at least a 90% bacterial count reduction on said poultry carcass, and in some aspects at least a 95% bacterial count reduction on said poultry carcass.

The desired period of time is often in the range of greater than 0 seconds to about 30 seconds, in certain aspects between about 1 second and about 20 seconds, in certain aspects between about 2 seconds and about 15 seconds, in certain aspects between about 3 seconds and about 10 seconds, and in certain aspects between about 4 seconds and about 8 seconds, with other subranges within the foregoing ranges contemplated. In some other aspects, the desired period of time is between about 1 second and about 30 seconds, in certain aspects between about 2 seconds and about 20 seconds, in certain aspects between about 3 seconds and about 15 seconds, and in certain aspects between about 3 seconds and about 10 seconds.

In some aspects, the poultry carcass is soaked, dipped, quenched, rinsed and/or washed after the picking stage and prior to the chilling stage in an intervention solution comprising an equilibrium peroxycarboxylic acid or a pH modified peroxycarboxylic acid.

After the intervention solution comprising an equilibrium peroxycarboxylic acid or a pH modified peroxycarboxylic acid is applied to the poultry carcass and/or poultry parts, the invention solution can be rinsed off the poultry carcass and/or poultry parts with water. Alternatively, after the intervention solution is applied, it is not subsequently rinsed off the poultry carcass and/or poultry parts prior to the chilling stage, such that the intervention solution is allowed to be left on the poultry carcass and/or poultry parts until an immersion chilling stage. In some aspects, the immersion chilling stage also contains an intervention solution, such as peroxyacetic acid.

In some aspects, after application of the intervention solution to the poultry carcass at an elevated temperature and an elevated concentration for a desired period of time according to certain aspects of the present invention, the poultry carcass is chilled to reduce the temperature to about 4° C.

EXAMPLES

As summarized in Table 1 below, ten chicken samples were treated with an elevated peroxyacetic acid concentration at an elevated temperature for a specified period of time using either an equilibrium peroxyacetic acid intervention solution or a pH modified peroxyacetic acid intervention solution. The chicken samples had a temperature of about 40° F. prior to treatment. The treated poultry carcasses were measured for the average bacterial count reduction as a result of the elevated peroxyacetic acid concentration and elevated temperature.

TABLE 1

Antimicrobial efficacy of elevated concentration and temperature application of PAA to poultry carcasses.

| PAA Concentration (ppm) | Temperature (° F.) | Exposure Time (seconds) | pH | Average % Reduction |
|---|---|---|---|---|
| 500 | 125 | 7 | ~3 | 77.26 |
| 500 | 125 | 7 | 7.7 | 93.68 |
| 500 | 72 | 10 | ~3 | 70.57 |
| 500 | 72 | 10 | 7.7 | 97.34 |
| 600 | 125 | 7 | ~3 | 61.94 |
| 600 | 125 | 7 | 7.7 | 89.34 |
| 700 | 125 | 7 | ~3 | 92.27 |
| 700 | 125 | 7 | 7.7 | 97.87 |

As shown in Table 1 above, poultry carcasses exposed to both an elevated PAA concentration and temperature for a period of time of at least 7 seconds experienced at least a 60% bacterial count reduction, in some aspects at least a 70% bacterial count reduction, in some aspects at least an 80% bacterial count reduction, in some aspects at least a 90% bacterial count reduction, and in some other aspects at least a 95% bacterial count reduction. As compared to equilibrium PAA intervention solutions at the same concentration, temperature and treatment time, pH modified PAA intervention solutions provided pronounced results.

These results illustrate the beneficial bacterial count reduction that results from contacting the poultry carcass with an intervention solution comprising a peroxycarboxylic acid at an elevated temperature and at an elevated concentration for a desired period of time of less than about 10 seconds. This reduction of bacterial count prior to a chilling stage is beneficial to the down-line processes in a processing plant, helping to improve quality and minimizing safety concerns relating to microbial contamination of the poultry product.

Various embodiments have been described herein. These embodiments are given only by way of example and are not intended to limit the scope of the claimed inventions. It should be appreciated, moreover, that the various features of the embodiments that have been described may be combined in various ways to produce numerous additional embodiments.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

The invention claimed is:

1. A method for the reduction in microbial activity in protein food products intended for human consumption, the method comprising:
    contacting said protein food products to an intervention solution comprising a peroxyacetic acid at an elevated concentration and elevated temperature for a desired period of time, said contact occurring after a picking stage and prior to a chilling stage;

wherein said elevated concentration being between about 200 ppm and about 5000 ppm;

wherein said elevated temperature being between about 100° F. and about 150° F.; and wherein said desired period of time being between about 1 second and about 30 seconds; and wherein said step of contacting said protein food products with said intervention solution comprising said peroxyacetic acid provides at least a 60% bacterial count reduction.

2. The method of claim 1, wherein said solution has a pH between about 3.0 and about 7.0.

3. The method of claim 1, wherein said solution has a pH between about 3.5 and about 5.5.

4. The method of claim 3, wherein said elevated concentration of the intervention solution is between about 300 ppm and about 2500 ppm of peracetic acid.

5. The method of claim 4, wherein said elevated temperature is between about 120° F. and about 135° F.

6. The method of claim 5, wherein said desired period of time is between about 3 seconds and about 10 seconds.

7. The method of claim 6, wherein said protein food product is a poultry carcass or poultry parts, wherein said contact step comprises soaking, dipping, quenching, rinsing or washing said poultry during poultry processing.

8. The method of claim 3, wherein said elevated temperature being between about 120° F. and about 135° F., said elevated concentration being between about 500 ppm and about 750 ppm of said peroxyacetic acid, and said desired period of time being between about 2 seconds and 10 seconds to result in at least an 80% bacterial count reduction.

9. The method of claim 1, wherein said solution has a pH between about 7.0 and about 10.0.

10. The method of claim 9, wherein said solution has a pH between about 7.5 and about 9.0.

11. The method of claim 9, wherein said elevated concentration of the intervention solution is between about 300 ppm and about 2500 ppm of peracetic acid.

12. The method of claim 11, wherein said elevated temperature is between about 120° F. and about 135° F.

13. The method of claim 12, wherein said desired period of time is between about 3 seconds and about 10 seconds.

14. The method of claim 10, wherein said elevated temperature being between about 120° F. and about 135° F., said elevated concentration being between about 500 ppm and about 750 ppm of said peroxyacetic acid, and said desired period of time being between about 2 seconds and 10 seconds to result in at least an 80% bacterial count reduction.

15. The method of claim 14, wherein said protein food product is a poultry carcass or poultry parts, wherein said contact step comprises soaking, dipping, quenching, rinsing or washing said poultry during poultry processing.

16. A method for the reduction in microbial activity in protein food products intended for human consumption, the method comprising:

contacting said protein food products to an intervention solution comprising a peroxyacetic acid at an elevated concentration and elevated temperature for a desired period of time at a pH between about 3.0 and 7.0;

wherein said elevated concentration being between about 400 ppm and about 1000 ppm;

wherein said elevated temperature being between about 115° F. and about 140° F.; and wherein said desired period of time being between up to about 30 seconds;

wherein said protein food product is a poultry carcass or poultry parts, wherein said contact step occurs after a picking stage and prior to a chilling stage and comprises soaking, dipping, quenching, rinsing or washing said poultry during poultry processing; and wherein said step of contacting said protein food products with said intervention solution comprising said peroxyacetic acid provides at least a 60% bacterial count reduction.

17. A method for the reduction in microbial activity in protein food products intended for human consumption, the method comprising:

contacting said protein food products to an intervention solution comprising a peroxyacetic acid at an elevated concentration and elevated temperature for a desired period of time at a pH between about 7.0 and 10.0;

wherein said elevated concentration being between about 350 ppm and about 1500 ppm;

wherein said elevated temperature being between about 110° F. and about 140° F.; and wherein said desired period of time being between up to about 30 seconds;

wherein said protein food product is a poultry carcass or poultry parts, wherein said contact step occurs after a picking stage and prior to a chilling stage and comprises soaking, dipping, quenching, rinsing or washing said poultry during poultry processing; and wherein said step of contacting said protein food products with said intervention solution comprising said peroxyacetic acid provides at least a 60% bacterial count reduction.

18. The method of claim 17, wherein said solution has a pH between about 7.5 and about 9.0.

19. The method of claim 17, wherein said elevated temperature being between about 115° F. and about 135° F., said elevated concentration being between about 400 ppm and about 750 ppm of said peroxyacetic acid, and said desired period of time being between about 1 second and about 20 seconds to result in at least an 70% bacterial count reduction.

20. The method of claim 17, wherein said elevated temperature being between about 120° F. and about 130° F., said elevated concentration being between about 500 ppm and about 750 ppm of said peroxyacetic acid, and said desired period of time being between about 2 seconds and about 15 seconds to result in at least an 80% bacterial count reduction.

* * * * *